(12) United States Patent
Huang (10) Patent No.: US 6,665,074 B2
(45) Date of Patent: Dec. 16, 2003

(54) INTERFEROMETRIC OIL-SPILL DETECTION SYSTEM

(76) Inventor: Yen-Chieh Huang, No. 16, Alley 5, Lane 54, Heping St., Yunghe City, Taipei 234 (TW)

( * ) Notice: Subject to any disclaimer, the term of this patent is extended or adjusted under 35 U.S.C. 154(b) by 0 days.

(21) Appl. No.: 09/982,467

(22) Filed: Oct. 17, 2001

(65) Prior Publication Data
US 2003/0072004 A1 Apr. 17, 2003

(51) Int. Cl.$^7$ ................................................ G01B 9/02
(52) U.S. Cl. ..................................................... 356/450
(58) Field of Search ........................ 356/70, 450, 517, 356/503, 504, 632

(56) References Cited

U.S. PATENT DOCUMENTS 6,031,615 A * 2/2000 Meeks et al. ............... 356/630

* cited by examiner

Primary Examiner—Samuel A. Turner
Assistant Examiner—Michael A. Lyons (57) ABSTRACT

An automatic, oil-spill-detection system, which employs thin-film and wavefront-splitting interference techniques to determines the existence of surface oil or oil drops in water is disclosed. Two independent automatic, decision-making systems are disclosed, which provide a reliable means for oil spillage detection. A computer code and a image extraction system are employed to discern and monitor the interference fringes generated from oil slicks. The computer-based imaging system can be further replaced by a compact and low-cost imaging circuit that functions reliably in a buoy with relatively low power consumption.

19 Claims, 9 Drawing Sheets

INTERFEROMETRIC OIL-SPILL DETECTION SYSTEM

FIELD OF THE INVENTION

The present invention is related to an oil-spill detection system, and more particularly to an interferometric oil-spill detection system.

BACKGROUND OF THE INVENTION

Oil spillage could occur in numerous locations such as seabed exploration sites, oil refineries, or areas close to oil tanks and pipelines. The loss of oil causes both capital and environmental damages. In particular, the environmental damage often takes a long period of time to recover. It is desirable to have an automatic oil spill detection system that monitors oil leaks in the early stage and transmits a suitable warning signal to dispatch a rescue effort for repair.

The existing oil spill detection schemes are mostly in two categories, the scanning type and the fixed-location type. The scanning type, usually satellite-based, monitors a large area of many square kilometers. For example the synthetic aperture radar (SAR) has a large coverage over seawater. The SAR imagery previously had some difficulty in distinguishing dark areas and lookalikes from oil spills. The fixed-location oil spill detectors are often buoyantly situated or anchored. Sometimes the buoy is set adrift but its coordinates are controlled by the global positioning system. These fixed-type oil-spill detectors monitor oil spills by chemical or optical means. Chemical reactions usually cause pollution themselves and chemicals are relatively difficult to maintain. Among the optical means, the generation of UV-induced fluorescence and the change of surface reflectivity on surface oil are the two existing oil-spill detection mechanisms. Unfortunately all of the existing detection schemes have one or several disadvantages, such as poor reliability, high power consumption, high cost, difficulties in maintenance, and complexity.

The SAR oil spillage detection technique is aimed for large-area monitoring while those fixed-location buoy detectors are suitable for real-time, prompt spillage warning at the deployed area. However, both the SAR oil detection technique and the fixed-location buoy detector have the disadvantages of high cost, difficulties in maintenance, and complexity. Therefore, it is desirable to design an early-warning type, surface-oil detector by using optical interferometric techniques. Unlike the existing optical schemes, the interferometric technique detects the interferometric images formed by oil thin films or by oil droplets. The interferometric image formation is more related to the oil geometry than its material property. Integrated into a compact circuit board, this technique is relatively simple, reliable, low-cost, and low-power consuming.

SUMMARY OF THE INVENTION

It is therefore an object of the present invention to provide an interferometric oil-spill detection system for detecting the existence of surface oil or oil drops in water.

It is further an object of the present invention to provide a relatively simple, reliable, low-cost, and low-power consuming oil-spill detection system.

It is further an object of the present invention to provide an interferometric oil-spill detection system for detecting the existence of oil spillage on a body of water by using interferometric techniques. The interferometric oil-spill detection system includes a light source for providing an incident light to the oil-spilled body of water, an image extraction device for receiving the reflected light from the oil-spilled body of water and recording the interference fringes of the reflected light, and an image process device connected to the image extraction device for determining whether oil spillage exists according to the interference fringes.

Preferably, the light source is an electromagnetic radiation source of any kind in the optical wavelength range. More preferably, the light source is a laser for providing coherent or partially coherent electromagnetic radiation. The light source consists of one or a few optical elements for collimating, focusing, defocusing, shaping, or directing the optical electromagnetic radiation to the body of water.

Preferably, the image extraction device is a one-dimensional charge-coupled-device (CCD) array sensor, or a CMOS linear sensor array, or a two-dimensional array of the same.

Preferably, the image process system is a computer having a computer program capable of processing the interference fringes and determining whether oil spillage exists.

It is further an object of the present invention to provide a method for detecting the existence of oil-spill on a body of water and transmitting a warning signal to dispatch a rescue effort for repair by using an oil-spill detection system comprising a light source, an image extraction device and an image process device. The method includes the steps of sending a light from the light source to the oil-spilled body of water, receiving the reflected light from the oil-spilled body of water, recording the interference fringes by the image extraction system, processing the interference fringes and checking whether the specific interference parameters are above the threshold values pre-programmed in the image process device, and thereby transmitting a warning signal to dispatch a rescue effort for repair when the specific interference parameters are above the pre-programmed threshold values.

In accordance with one aspect of the present invention, the specific interference parameters are fringe intensity, infringe width, and the number of fringes detected from the image sensor.

It is further an object of the present invention to provide an oil-spill detection system for detecting the existence of oil spillage on a body of water by interferometric techniques. The oil-spill detection system includes a light source system and a discerning medium. This light source system includes a light source and one or a few lenses for providing an incident light to the oil-spill on the water of body. The discerning medium has an image sensor for receiving the reflected light from the oil-spilled body of water, and a logic circuit connected to the image sensor for processing the interference light to determine whether oil spillage exists according to the existence of the interference fringes.

Preferably, the discerning medium is an integrated circuit element, which includes the image sensor and a logic circuit monolithically integrated in a semiconductor chip or a compact circuit board similar to the size of a computer interface card powered by a low-voltage power supply or a solar battery.

More preferably, the light source system and the discerning medium are fabricated monolithically in a semiconductor circuit chip or a compact circuit board similar to the size of a computer interface card powered by a low-voltage power supply or by a solar battery.

Preferably, the light source is any coherent, partially coherent, or incoherent electromagnetic radiation source generating radiations at the optical wavelengths.

Preferably, the light source is a laser of any kind providing coherent or partially coherent electromagnetic radiation.

Preferably, the image sensor is a one-dimensional CCD array sensor, or a CMOS linear sensor array, or a two-dimensional array of the same.

It is further an object of the present invention to provide a method for detecting the existence of oil-spill on a body of water and transmitting a warning signal to dispatch a rescue effort for repair by using an oil-spill detection system comprising a light source and a discerning medium, wherein the discerning medium has an image sensor and a logic circuit. The method includes the steps of transmitting an incident light from the light source to an oil-spilled body of water, receiving the reflected light from the oil-spilled body of water by the image sensor of the discerning medium, processing the interference fringes formed by the reflected light and checking whether the specific interference parameters are above the threshold values pre-programmed in the logic circuit of the discerning medium, and thereby transmitting a warning signal to dispatch a rescue effort for repair when the specific interference parameters are above the threshold values.

Preferably, the specific interference parameters are fringe intensity, infringe width, and the number of fringes.

The present invention utilizes two light interference mechanisms, the thin-film interference and the wavefront-splitting interference. It may be best understood through the following descriptions with reference to the accompanying drawings, in which:

DETAILED DESCRIPTION OF THE PREFERRED EMBODIMENT

In general, oils on a body of water are of two kinds, one with its surface tension smaller than water and one with its surface tension larger than water. The one with a smaller surface tension spreads itself into an oil thin film above the water surface, whereas the other with a larger surface tension often forms oil drops in water. For example, gasoline spreads itself quickly into a thin film above water and heavy engine oil sometimes forms droplets. The interferometric techniques for detecting both types of oil spillage on a water surface is delineated in the following.

A thin layer of oil on a water surface may generate rainbow-type interference fringes when viewed under the sun, a broadband white light source. This phenomenon is often observed routinely in one's life. It results from the well-known thin-film interference, where the reflected light from the oil surface interferes with that from the water surface below the oil film. Because the sun is a white light source, one observes constructed interference of different colors at different angles. When incident by a narrow-band coherent light source, like a laser, the interference image is even more pronounce, interleaved with bright and dark stripes corresponding to the constructive interference and destructive interference at that particular wavelength. Thin-film interference occurs only when the refractive index of the film differs from those sandwiching the film.

Figure 1:
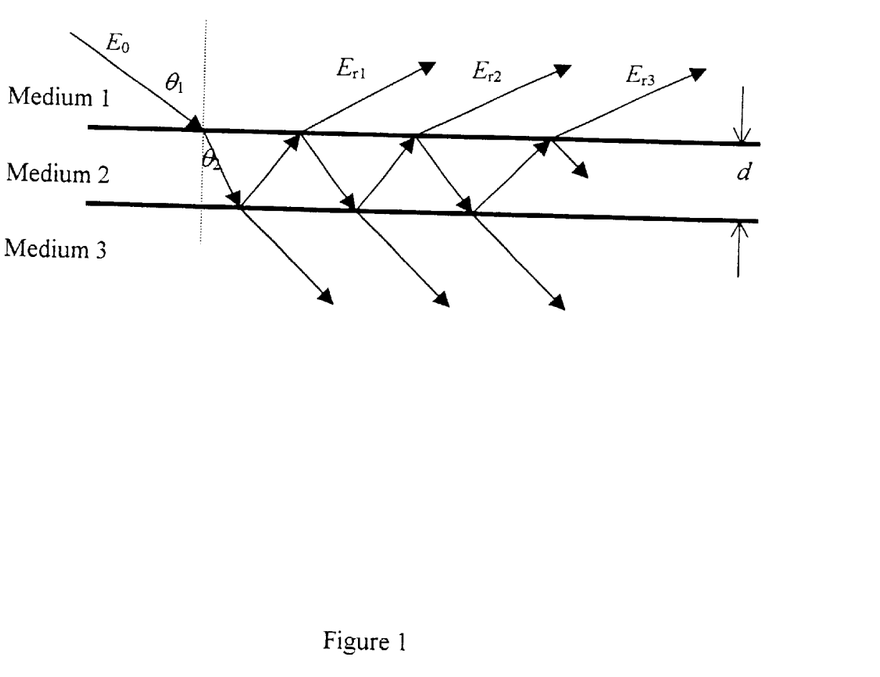
FIG. 1 is the configuration for performing the thin-film interference calculation according to the present application, wherein the three media are air, oil, and water, respectively, and the total reflected optical field is the sum of all individual reflected fields, $E_{r1}, E_{r2}, E_{r3} \ldots$ ($\theta_1$ is the incident angle in the medium 1 and $\theta_2$ is the refractive angle in the medium 2)

FIG. 1 illustrates the scattering configuration for the theoretical calculation according to the present application, wherein a monochromatic light is incident from the medium 1 toward the medium 3 with the thin film, the medium 2, sandwiched in between. By performing the standard infinite-sum calculation for the successive reflected field, $$E_r = E_{r1} + E_{r2} + E_{r3}$$

the reflectance expression as following is obtained, $$R = \frac{I_r}{I_0} = \frac{\left(\frac{\rho_{23} - \rho_{21}}{1 - \rho_{21}\rho_{23}}\right)^2 + F\sin^2\frac{\delta}{2}}{1 + F\sin^2\frac{\delta}{2}}, \quad (1)$$

where $$F = \frac{4\rho_{21}\rho_{23}}{(1 - \rho_{21}\rho_{23})^2}$$

is the coefficient of finesse, $\delta$ is the optical phase difference between successive reflections, $\rho_{mn}$ is the reflection coefficient when light is incident from the medium m to the medium n. The phase difference is given by $$\delta = \frac{2\pi}{\lambda_0} 2dn_2\cos\theta_2,$$

$\cos\theta_2$, where $\lambda_0$ is the free-space wavelength of the incident light, d is the thin film thickness, and $\theta_2$ is the refractive angle in the medium 2. The refractive angle $\theta_2$ can be found from Snell's law with a known incident angle $\theta_1$ in the medium 1. If the medium 1 and medium 3 are the same materials and therefore $\rho_{21}=\rho_{23}$, the reflectance in Eq. (1) is reduced to the well-known etalon formula $$R = \frac{I_r}{I_0} = \frac{F\sin^2\frac{\delta}{2}}{1 + F\sin^2\frac{\delta}{2}}. \tag{2}$$

Figure 2:
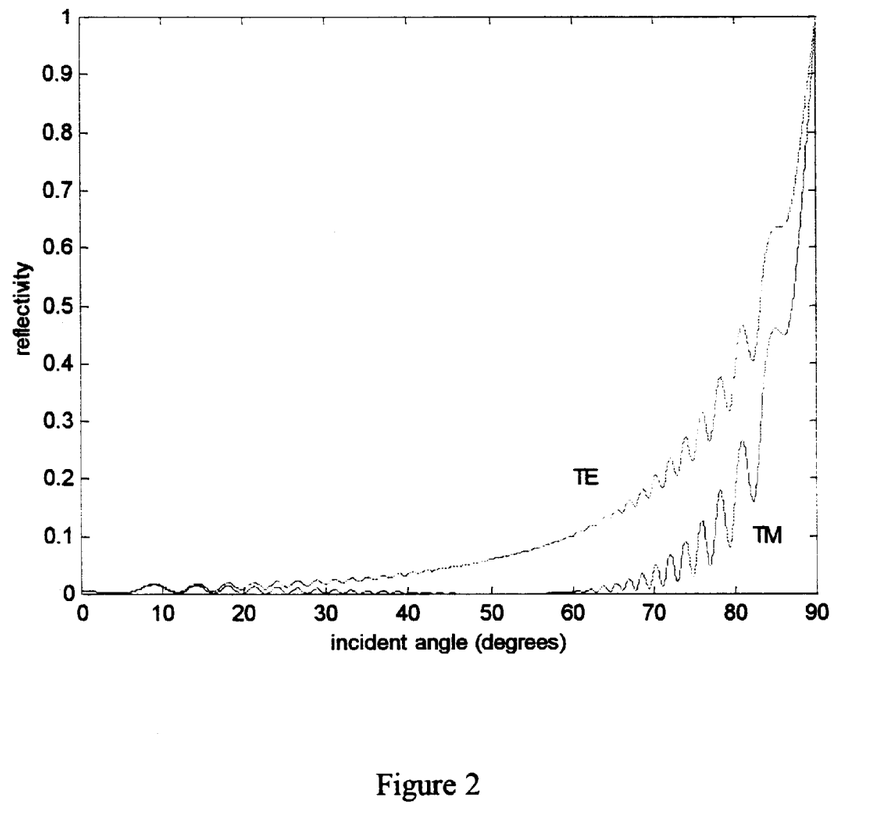
FIG. 2 is a computer simulation of the thin-film interference fringe intensity versus the incident angle for TE and TM incident waves, wherein the refractive indices of the three media in this example are $n_1=1$ (air), $n_2=1.1$ (oil), $n_3=1.3$ (water), and the gasoline film thickness is assumed to be 20 $\mu$m.

In the etalon formula, the contrast or visibility of the reflected image is always 100%, because the destructive interference reflects no light to the medium 1. However, for the case of three medium layers, the reflected light from the medium 3 can not completely cancel the light refected from the medium 1 in its destructive phase. Therefore the visibility of the reflection fringes from an oil thin film sandwitched between air and water is not as good as an etalon, depending on the difference among the refractive indices of the three media. Furthermore the reflection coefficients $\rho_{21}$ and $\rho_{23}$ are functions of light polarization, as can be seen from the Fresnel equations. FIG. 2 illustrates the reflectance versus the incident angle calculated from Eq. (1) for a TM incident wave and a TE incident wave. The TE incident wave has its electric field polarized normal to the plane of FIG. 1 and the TM incident wave has its electric field polarized in the plane of FIG. 1. The refractive indices of the three media in the calculation are $n_{=1}=1$ (air), $n_2=1.1$ (October 1995 unleaded gasoline, Chinese Petroleum Corp.), and $n_3=1.3$ (water). The thickness of the gasoline layer at a certain location varies over the time course of oil spillage, depending on the amount of gasoline in that area. In FIG. 2, a thickness d=20 $\mu$m is arbitrarily choosen to illustrate a typical situation. The number of interfernce fringes in FIG. 2 increases with the thickness of the oil layer over a fixed range of the incident angle. For TM-wave incidence, no light is refected at the Brewster angle near 48°. However, it is evident that TM polarization shows more intensity modulation and thus gives better visibility.

When the refactive indices of the oil and water are not much different, the reflectance expression (1) reduces to $$R = \frac{I_r}{I_0} \approx \rho_{21}^2 + 4\rho_{21}\rho_{23}\sin^2\frac{\delta}{2}$$

with the approximation $\rho_{23}\approx 0$ and $|\rho_{21}|\gg|\rho_{23}|$. It is straightforward to show that the visibility becomes $$V = \frac{I_{r,\max} - I_{r,\min}}{I_{r,\max} + I_{r,\min}} \approx 2\left|\frac{\rho_{23}}{\rho_{21}}\right| \approx 0.$$

Figure 3:
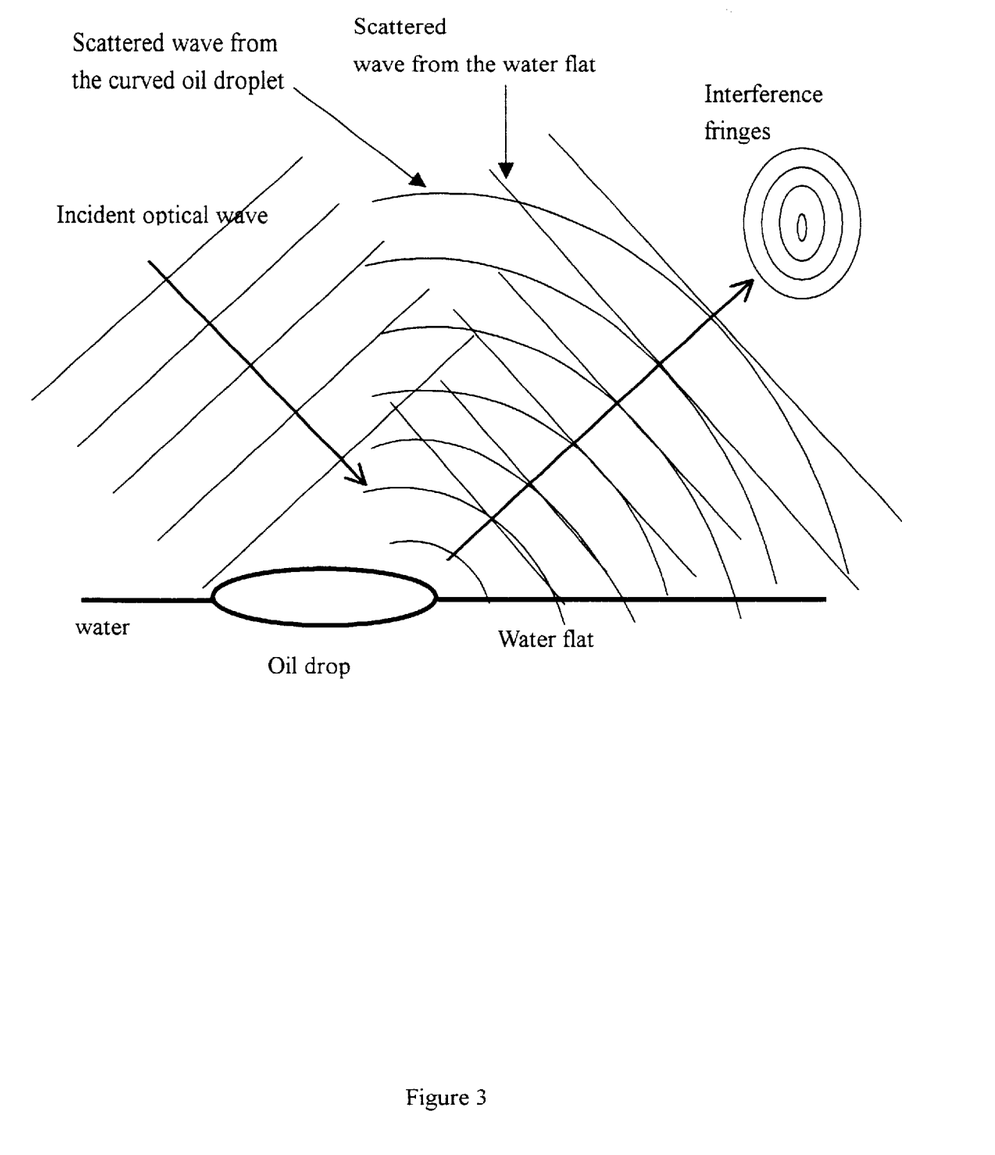
FIG. 3 is the schematic illustration of wavefront-splitting interference resulting from an oil drop.

Therefore the thin-film interference fringes might not be discernible by an image recording aparatus when the refractive indices of the second and third media are very close to each other. However, highly visible interference fringes were observed in the experiment according to the present invention, when the medium 2 was the Castrol 10W-60 engine oil with its refractive index n=1.4 and the medium 2 water with its refractive index n=1.3. The interference fringes result from the splitting of the laser wavefront at the joint of the oil and water interface, as FIG. 3 illustrates. In particular, some oil has a larger surface tension, forming a curved surface at the edge immediately next to a water flat. The radius of curvature of the curved surface, typically less than a millimeter, can be much smaller than that of the laser wavefront if the laser source is placed far away or the laser beam diverges quickly. Therefore, the reflected wave is approximately a superposition of a plane wave and a wave with its wavefront conforming to the curved oil edge. These two waves form an interference pattern in the far field. Because the refractive indices of the oil and water are close to each other, the visibility of the interference pattern is nearly 100%. The mechanism is in fact similar to the wavefront-splitting interference. As shown in FIG. 3, a curved wavefront and a nearly plane-wave wavefront, derived from a single laser wavefront at the joint of oil and water, interfere with each other in the far field.

For oils with a small surface tension, the same technique applies as well. When oil starts to spread from a high concentration area on a water surface, it moves with a curved edge in the depth direction and eventually forms a thin oil layer on water. As an early warning system, this technique is capable of picking up the interferene signal at the initial phase of oil spread. Moreover, surface oil is often broken into many dorplets or islands under a shaky water environment, and those oil droplets and islands can be effective scattering centers for wavefront-splitting interferometry.

Figure 4:
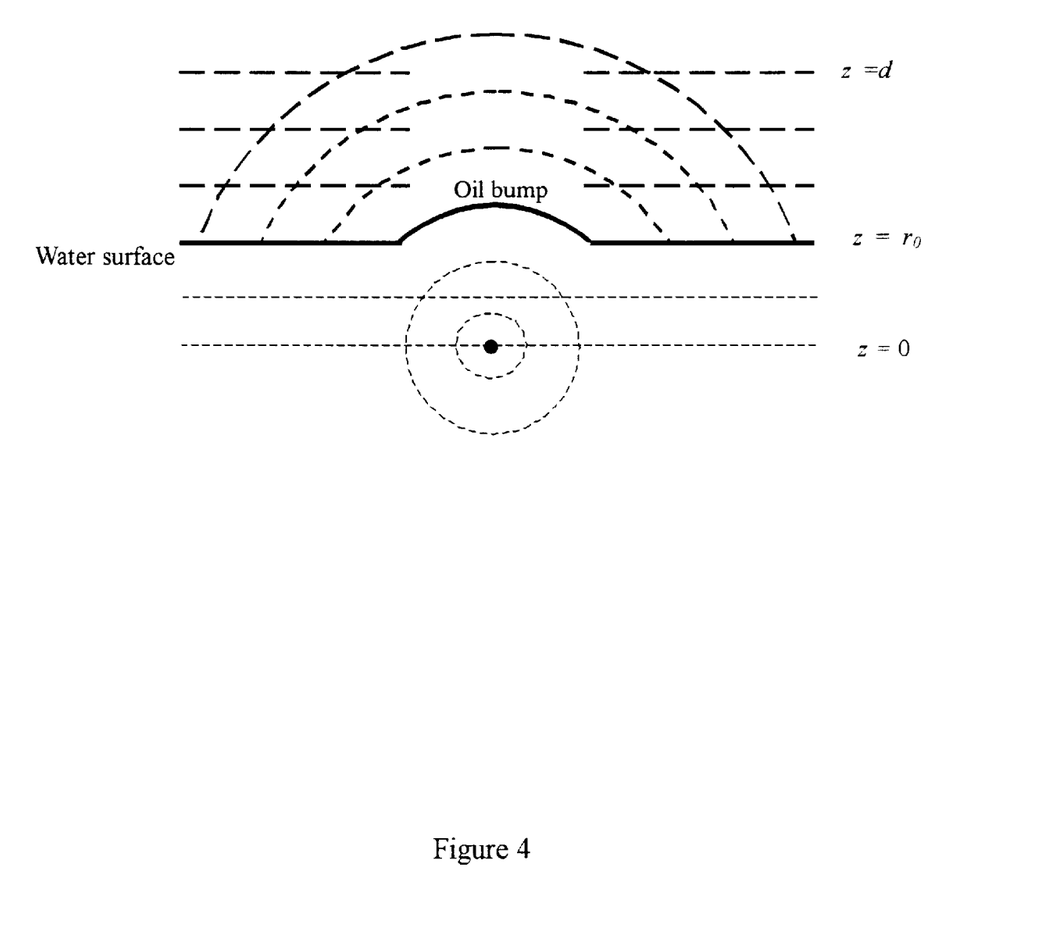
FIG. 4 is the scattering configuration for modeling the wavefront-splitting interference, wherein a plane wave is incident normally in the—z direction onto a oil bump, the reflected wave is approximately a superposition of a plane wave and a spherical wave.

The interference can be best appreciated by summing a plane wave and a spherical wave. FIG. 4 shows this simplified configuration, where a plane wave is incident normally to a spherical oil bump of radius r above a water surface. The dark dashed lines above the water surface represent the wavefronts of the plane wave and the spherical wave, and the thin dashed lines are the virtual wavefronts originating from the spherical center of the oil bump. In the far field z=d, the scattered field is approximately the superpostion of a plane wave and a spherical wave, originating at a distance $r_0$ below the water surface at z=0. At large d, the spherical wave can be approximated by a paraboloidal wave, given by the phasor representation $$E_s = \sqrt{I_0}\exp\left[-jkd - jk\frac{r^2}{2d}\right], \tag{3}$$

where $I_0$ is the normalized intensity of the laser at z=d, r is the distance from the z axis, $j=\sqrt{-1}$ is the imaginary unit, and $$k = \frac{2\pi}{\lambda}$$

is the wavenumber. Assuming that the plane wave field at z=d has a comparable intensity, one obtains its phasor representation $$E_p=\sqrt{I_0}exp[-jkd] \tag{4}$$

The total intensity at z=d is therefore $$I(z=d) = |E_s + E_p|^2 = 4I_0\cos^2\left(k\frac{r^2}{4d}\right). \tag{5}$$

Equation (5) predicts the N-th constructive interference ringe at the radius of $$r_N=\sqrt{2d\lambda N} \tag{6}$$

Figure 5:
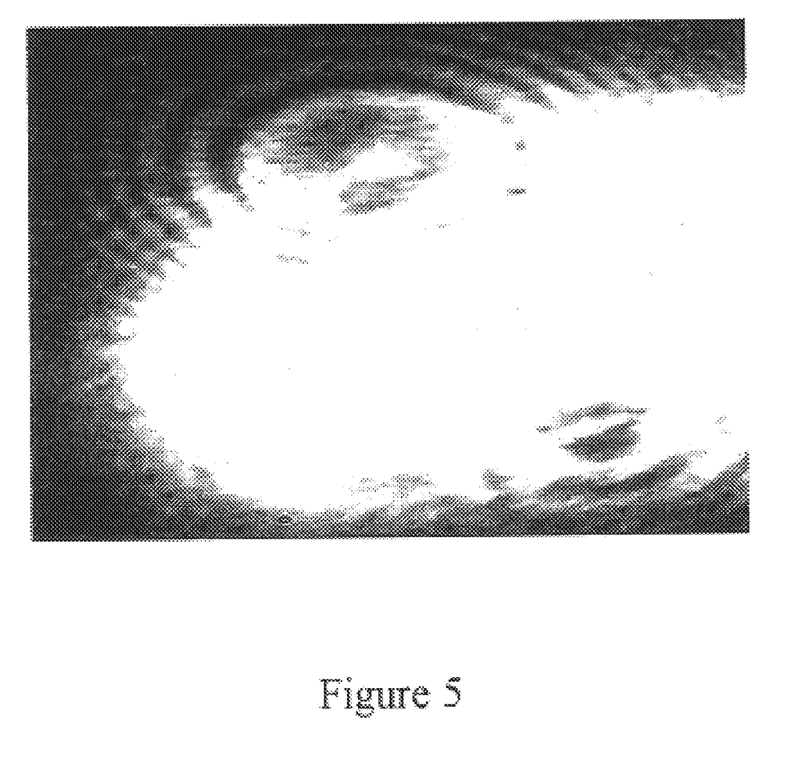
FIG. 5 is a typical wavefront-splitting interference image resulting from a real oil drop in the experiment.

The constructive interference at z=d forms a series of bright rings with a reducing separation in r. For example, to have $r_1=1$ mm for $\lambda=670$ nm, d is about 75 cm. If the image plane is 30 cm above the water surface, the radius of curvature of the oil bump is 45 cm. Those highly visible rings with their shape mimicing the oil drop were frequently observed in the experiment of the present invention. FIG. 5 shows a typical interference image, in which the laser incident angle is 80° with respect to the normal of the water surface, the laser wavelength is 670 nm, and the distance between the water surface and the image plane is 30 cm. The oil drop was formed by the Castrol 10-60W engine oil with a measured refractive index of 1.4.

Figure 6:
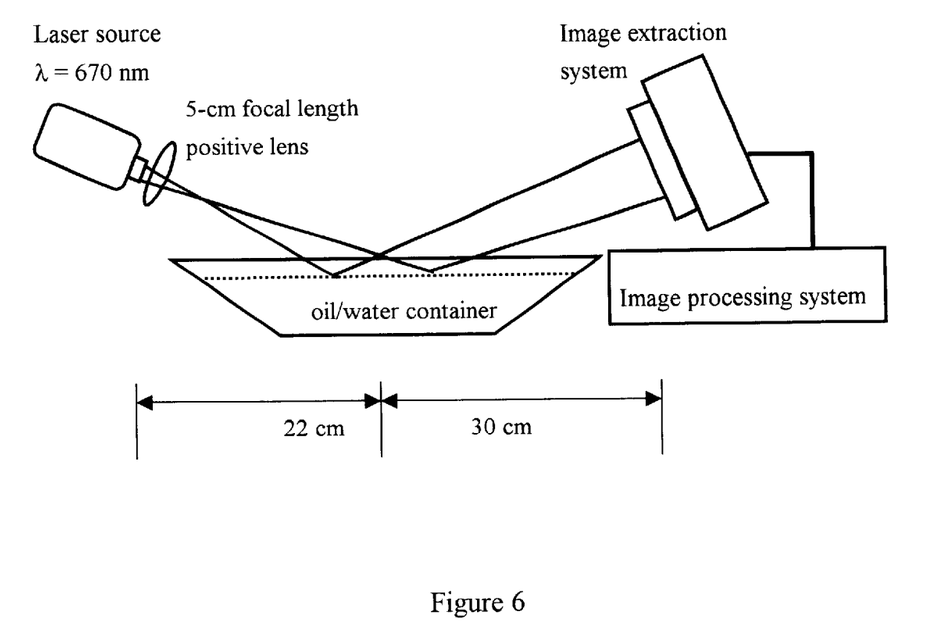
FIG. 6 is a schematic view showing a oill-spill detection system according to the preferred embodiment of the present invention.

FIG. 6 illustrates the oil-spill detection system according to the preferred embodiment of the present invention, where a 670 nm-wavelength diode laser module (made by Simpatico Co. Ltd) is the light source, an image extraction device records the interference fringes, and the image process system determines whether oil spillage exists. Since the oil film thickness is so thin that the interference fringes can even be viewed under a white light source, the coherence length of the laser source is relatively not important. The diode laser module consists of a 6.4 mW, 670 nm laser diode and an aspherical lens positioned at 1 cm in front of the diode. The aspherical lens has a 3-mm diameter aperture, preserving the central part of the laser wavefront and clipping 60% of the laser diode power to make a circular beam. Since the lens aperture only transmits a small portion of the diode laser wavefront, the laser module produces a 2.5 mW, nearly flattop, circular beam with a half divergent angle of 0.5 mrad in both transverse directions. To expand the laser beam, a 5-cm focal length, double convex lens is installed at a 3-cm distance from the aspherical lens. A 2.5-cm diameter, circular laser beam is generated on the image screen (not shown). The distance between the diode laser module and the water surface is 22 cm and that between the water surface and the image screen is 30 cm, as shown in FIG. 6. The laser waist, after the focusing lens, is about 14 cm from the water surface. Therefore the radius of curvature of the laser wavefront is much larger than that of the curved oil edge, which allows the wavefront splitting interference to be modeled by using a plane wave and a spherical wave in the previous section. In this experiment, the laser incident angle is about 75° relative to the normal of the water surface. At this incident angle, the laser beam has an elliptical beam profile on the water surface with its major axis=3.8 cm and its minor axis=1 cm.

In the imaging experiment of the present invention, a charged-coupled-device (CCD) camera is firstly employed as the image extraction device. The CCD signal is connected to a National Instrument IMAQ image capture board installed in a computer (i.e. image process system). A LabView™ computer code processes the recorded image, and determines whether the image is indeed an interference fringe pattern. In the second phase of the experiment, according to the present invention, the whole imaging and discerning system is replaced with a CMOS linear sensor array connected to a compact, integrated, logic circuit.

Figure 7:
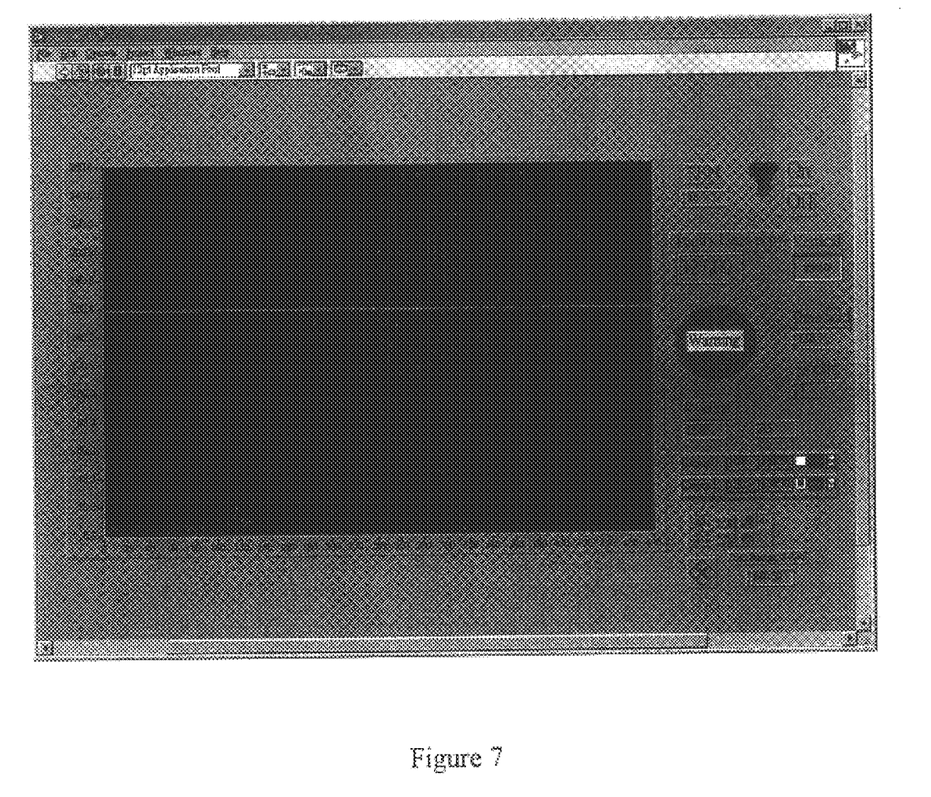
FIG. 7 shows the output of the preferred oill-spill detection system on a LabView™ computer platform, wherein the horizontal axis is the position coordinate of the interference fringes, the vertical axis is the fringe intensity (both in arbitrary units), the threshold intensity is set at 160 in the vertical scale, the threshold fringe width is set at 4 in the horizontal scale, and the threshold number of qualified interference fringes is set at 10, as shown in the T.P.N. box.

In the CCD-LabView™ system (i.e. the oil-spill detection system) of the present invention, a National Instrument IMAQ card captures the CCD image and displays the interference fringes on a computer. It is necessary to program the LabView™ such that the computer is capable of scanning the intensity signal linearly both in the vertical and horizontal directions throughout the two-dimensional image. During the scanning process, the program automatically checks three threshold parameters, the fringe intensity, the fringe width, and the number of fringes. The threshold values set the least condition of sending out a warning signal in the event of oil spillage. Checking the fringe intensity ensures that the image signal is above the noise level and checking the other two parameters guarantees the existence of interference fringes. The linear scan sends out a warning signal whenever it detects a set of interference fringes that satisfies all three threshold values. FIG. 7 shows a typical computer output of the detection system according to the present invention, where the horizontal axis of the window is the position coordinate of a one-dimension image sample from the CCD camera and the vertical axis is the intensity of that particular sample. The units are arbitrary. The horizontal line intercepting the intensity signal sets the intensity threshold at 160 in the vertical scale. For this particular case, the threshold fringe width is 4 in the horizontal scale, and the threshold number of qualified interference fringes is 10, as shown in the T.P.N. box. In FIG. 7, the automatic scanning process returns a result of 15 qualified interference fringes, as the # Found box shows. The warning button lights up whenever the scanned sample satisfies all three threshold values. The LabView™ program of the present invention has the full flexibility in presetting the three threshold values, according to the field conditions.

In order to minimize the size and cost, the CCD camera and the image-processing computer can be replaced by a discerning circuit board. The circuit board consists of a Hamamatsu N-MOS linear image sensor (S3923-256Q) and a logic circuit for checking the three threshold parameters given previously. In the embodiment, the circuit board is powered by a 5 Volt DC power supply and its overall size is similar to a typical computer interface card.

Figure 8:
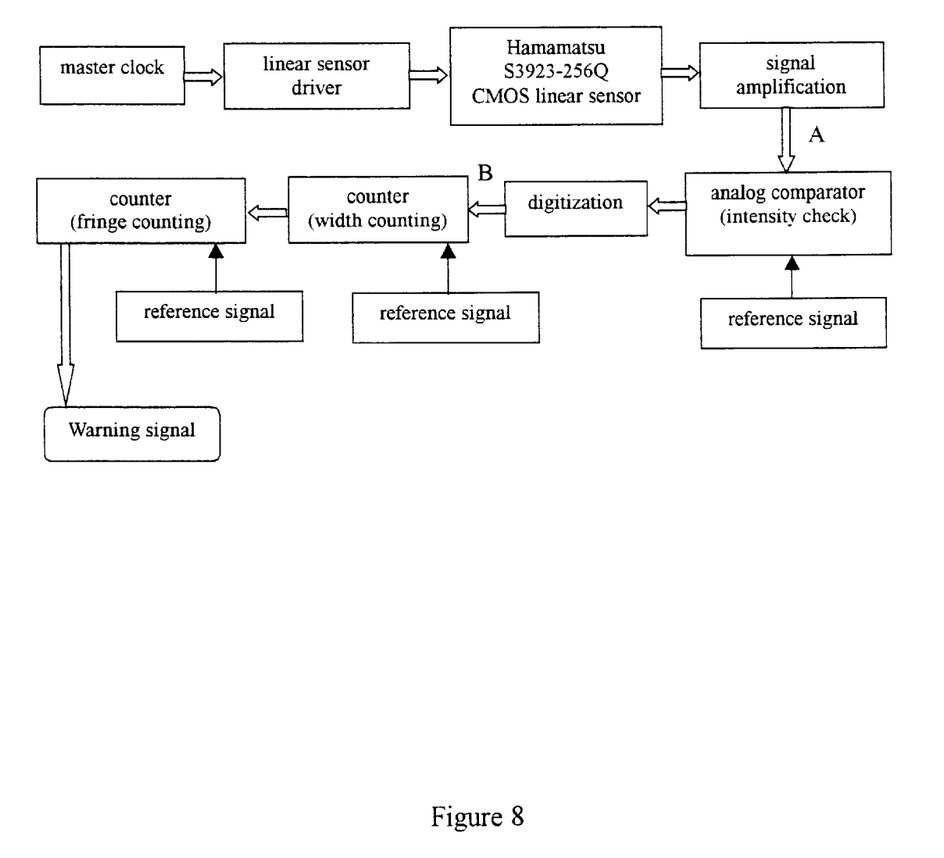
FIG. 8 is the data processing flowchart of a discerning circuit according to another preferred embodiment of the present invention.
Figure 9:
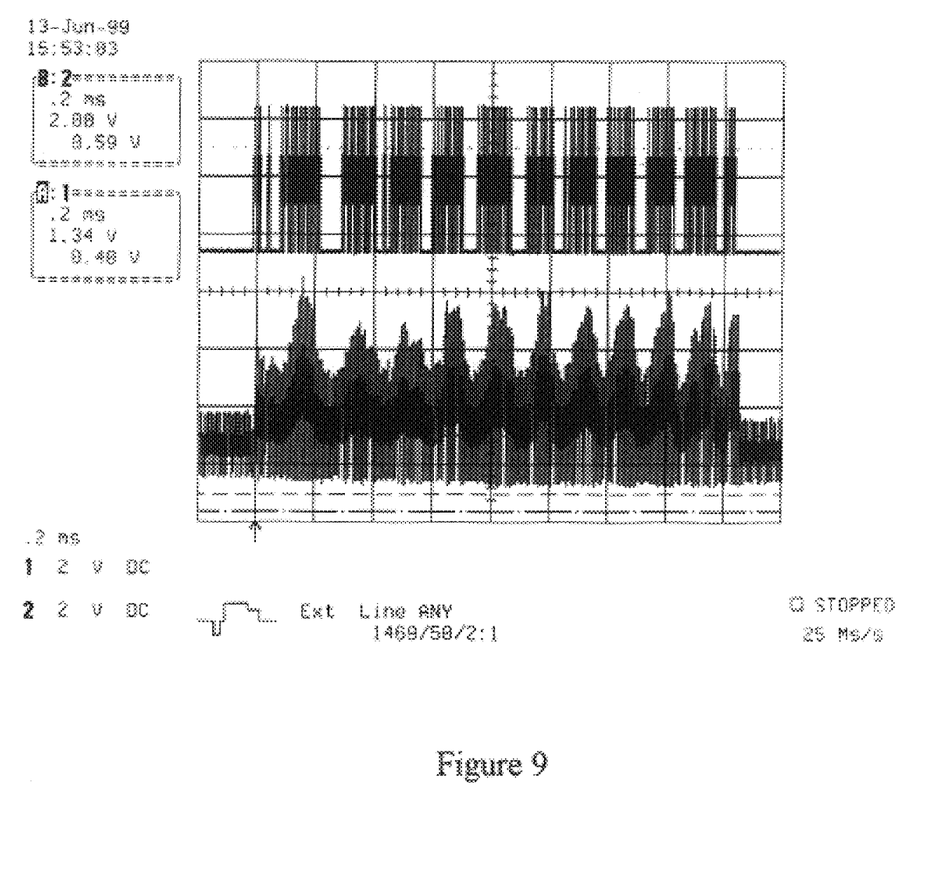
FIG. 9 shows a typical interference fringe signals before and after digitization, wherein the lower trace shows the amplified fringe signals at Point A of FIG. 8, and the upper trace is the digitized fringe signal at Point B of FIG. 8.

A 250 kHz, 50% duty-cycle, 2.5 Volt square wave serves as the master clock of the Hamamatsu image sensor. A 100 Hz, 50% duty cycle square wave modulates the 250 kHz master clock to separate independent measurements. In each of the 10 msec period, one cycle of the 100 Hz, the interference intensity information is extracted by the Hamamatsu linear image sensor, amplified in an operational amplifier, and analyzed by three logic stages for threshold value checking. FIG. 8 is the data flowchart of the circuit according to the present invention, and FIG. 9 shows the output waveforms at the points A and B in FIG. 8. The lower trace of FIG. 9 illustrates the amplified interference signal taken by the linear image sensor, corresponding to the point A in FIG. 8. The upper trace of FIG. 9 shows the digitized intensity at the points B in FIG. 8. The closely packed lines are square waves of the 250 kHz master clock. The digitized intensity is set to 5 volt if the signal at the point A is higher than the pre-programmed threshold value and is otherwise set to zero. The digitized intensity then goes though two more logic stages to check the fringe width and the number of qualified fringes. If the signal satisfies all the three logic checks, an oil spillage warning signal is sent to a radio beeper for subsequent actions. All the electronics are commercial-grade, low-cost, and low-power integrate circuit chips, such as CMOS 4538B, 4047, 4040, 4064, 40174, and the like.

The threshold values are programmable through three reference voltages, subjected to the field conditions and the optical design. In general, the intensity threshold voltage value can be set at a value slightly higher than the background noise. The background noise is the signal voltage measured without the oil thin film. A preferred intensity threshold voltage is set 20% above the background noise. The upper limit of the intensity threshold voltage ought to be less than the signal voltage. Typically a signal-to-noise ratio larger than two is obtained. Optical design determines the threshold values of the fringe width and the number of fringes. For example, if the optics is designed such that the laser incident angle is 75 degrees and the laser beam has a full divergence angle of 10 degrees, the threshold value of the number of fringes can be ~5 for a TM incident field, as indicated in FIG. 2. It is assumed that the material parameters used in FIG. 2 are still valid for this example. The threshold value of the fringe width is approximately the multiplication of the fringe angular width and the distance between the imaging apparatus and the water surface. For example, near the 75-degree incident angle, the fringe angular width is about 1 degree in FIG. 2 and the fringe spatial width should be ~5 mm for a 30-cm separation between the water surface and the imaging apparatus. If the interference fringes are primarily from wavefront-splitting interference, the threshold values can be inferred in a similar fashion.

In natural water, tidal waves may disturb the signal extraction in a buoyant optical system. If each measurement event is faster than the time constant of water motion, the water surface is considered static by the electronics circuit. Since the surface water wave usually conducts low-frequency motion, the 100 Hz data refreshing rate is adequate for most situations. If necessary, the 100 Hz data rate can be increased to avoid the problem of water motion.

Oil spillage with unleaded gasoline and engine oil in a water tank is experimentally simulated. The success rate of detecting oil spillage is nearly perfect. The image sensor array circuit performs equally well as does the CCD-LabView™ system. As an early warning system, this technique is designed to provide oil spill detection before the oil spreads into a large area. Occasional failure occurs when the engine oil forms a thick and smooth oil layer in the water tank. Under this circumstance, no water-oil interface is available to generate wavefront-splitting interference fringes, and the oil layer is too thick to generate well-separated thin-film interference fringes. However, small air bubbles are often present in the thick oil layer, which are in fact excellent scattering centers for generating wavefront-splitting interference fringes.

An optical early warning system for monitoring oil spillage has been successfully implemented according to the present invention. The system takes advantage of the thin-film interference and wavefront-splitting interference from the oil and water interfaces. In particular, the wavefront-splitting interference gives excellent fringe visibility even when the refractive indices of water and oil are close to each other. In addition, two detection systems, a CCD/LabView system and a sensor-array/logic-circuit system have also been tested. Both systems show excellent reliability and flexibility in discerning the interference fringes resulting from oil slicks. The sensor-array/login-circuit detection system is compact, low-cost, low power consuming, and can be installed in a stand-alone buoy with ease.

While the invention has been described in terms of what are presently considered to be the most practical and preferred embodiments, it is to be understood that the invention need not be limited to the disclosed embodiment. On the contrary, it is intended to cover various modifications and similar arrangements included within the spirit and scope of the appended claims which are to be accorded with the broadest interpretation so as to encompass all such modifications and similar structures. Therefore, the above description and illustration should not be taken as limiting the scope of the present invention which is defined by the appended claims.

What we claim is:

1. An interferometric oil-spill detection system for detecting the existence of oil spillage on a body of water by interferometric techniques, comprising:
    a light source for providing an incident light to said oil-spilled body of water;
    an interference-fringe recording device for receiving the reflected light from said oil spillage and said body of water and recording the interference fringes; and
    an interference-fringe processing device connected to said interference-fringe recording device for determining whether said oil spillage exists according to said interference fringes.

2. The interferometric oil-spill detection system according to claim 1, wherein said light source is an optical spontaneous emission source.

3. The interferometric oil-spill detection system according to claim 1, wherein said light source is an optical stimulated emission source called a laser.

4. The interferometric oil-spill detection system according to claim 3, wherein said light source comprises:
    a laser for providing said incident light; and
    a light manipulating system, containing at least one optical lens for collimating, focusing, defocusing, shaping, and directing said incident light to said body of water.

5. The interferometric oil-spill detection system according to claim 1, wherein said interference-fringe recording device is a charged-coupled device (CCD) for image recording.

6. The interferometric oil-spill detection system according to claim 1, wherein said interference-fringe recording device is one selected from a group consisting of one-dimensional charged-coupled device (CCD) array sensor, a CMOS linear sensor array and a two-dimensional array of the same.

7. The interferometric oil-spill detection system according to claim 1, wherein said interference-fringe processing device is a computer having a computer program capable of processing said interference fringes and determining whether said oil spillage exists.

8. A method for detecting the existence of oil spillage on a body of water and transmitting a warning signal to dispatch a rescue effort for repair by using an oil-spill detection system comprising a light source, and image extraction device and an image process device, comprising the steps of:
    sending an incident light from said light source to said oil-spilled body of water;
    receiving the reflected light from said oil spillage and said body of water,
    and recording the interference fringes by said image extraction system; and
    processing said interference fringes to determine whether said oil spillage exists and checking whether the specific interference parameters are above the threshold values by said image process device, and thereby transmitting a warning signal to dispatch a rescue effort for repair when said specific interference parameters are above the threshold values.

9. The method according to claim 8, wherein said specific interference parameters are fringe intensity, infringe width, and the numbers.

10. An oil-spill detection system for detecting the existence of oil spillage on a body of water by interferometric techniques, comprising:
    a light source for providing an incident light to said oil-spilled body of water;
    an interference-fringe discerning medium, said interference-fringe discerning medium having an image sensor for receiving the reflected light from said oil spillage and said body of water, and a logic circuit connected to said image sensor for processing the interference fringes formed by said reflected light determine whether said oil spillage exists according to said interference fringes.

11. The interferometric oil-spill detection system according to claim 10, wherein said interference-fringe discerning medium is an integrated circuit element.

12. The interferometric oil-spill detection system according to claim 11 wherein said integrated circuit element has a size similar to a computer interface card.

13. The interferometric oil-spill detection system according to claim 11, wherein said integrated circuit element includes said image sensor and said logic circuit monolithically integrated in a semiconductor chip and a compact circuit board.

14. The interferometric oil-spill detection system according to claim 10, wherein said light source is an optical spontaneous emission source.

15. The intrferometric oil-spill detection system according to claim 10, wherein said light source is a optical stimulated emission source, called a laser.

16. The interferometric oil-spill detection system according to claim 15, wherein said light source comprises:
  a laser for providing said incident light; and
  a light manipulating system, containing at least one optical lens for collimating, focusing, defocusing, shaping, and directing said incident light to said body of water.

17. The interferometric oil-spill detection system according to claim 10, wherein said image sensor is a CMOS linear sensor array.

18. The method for detecting the existence of oil spillage on a body of water and transmitting a warning signal to dispatch a rescue effort for repair by using an oil-spill detection system comprising a light source and a discerning medium, wherein said discerning medium has an image sensor and a logic circuit, comprising the steps of:
  sending an incident light form said light source to said oil-spilled body of water;
  receiving the reflected light from said oil-spill and said body of water by said image sensor of said discerning medium; and
  processing the interference fringes formed by said reflected light to determine whether said oil spillage exists and checking whether the specific interference parameters are above the threshold values by said logic circuit of said discerning medium, and thereby transmitting a warning signal to dispatch a rescue action for repair when said specific interference parameters are above the threshold values.

19. The method according to claim 18, wherein said specific interference parameters are fringe intensity, infringe width, and the number of fringes.

* * * * *